United States Patent

Von Behrens et al.

[11] Patent Number: 5,983,735
[45] Date of Patent: *Nov. 16, 1999

[54] METHOD AND APPARATUS FOR ANALYZING PARTICULATE MATTER

[75] Inventors: Wieland E. Von Behrens, Dallas; Roger Bourree, Cedar Hill; George Chappell, DeSoto; James G. Young, Grand Prairie, all of Tex.

[73] Assignee: MWI, Inc., Dallas, Tex.

[ * ] Notice: This patent is subject to a terminal disclaimer.

[21] Appl. No.: 09/144,716

[22] Filed: Sep. 1, 1998

Related U.S. Application Data

[63] Continuation of application No. 08/741,980, Oct. 31, 1996
[60] Provisional application No. 60/006,917, Nov. 17, 1995.

[51] Int. Cl.[6] .................................................. G01N 27/00
[52] U.S. Cl. ............................................................. 73/865.5
[58] Field of Search .......................... 73/865.5; 356/441, 356/442; 324/71.4; 377/11

[56] References Cited

U.S. PATENT DOCUMENTS

| | | | |
|---|---|---|---|
| Re. 28,558 | 9/1975 | Hogg . | |
| 2,656,508 | 10/1953 | Coulter | 324/71 |
| 3,299,354 | 1/1967 | Hogg | 324/71 |
| 3,746,976 | 7/1973 | Hogg | 324/71 |
| 3,793,587 | 2/1974 | Thom et al. | 324/71 |
| 3,810,010 | 5/1974 | Thom | 324/71 |
| 3,871,770 | 3/1975 | von Behrens et al. | 356/103 |
| 3,902,115 | 8/1975 | Hogg et al. | 324/71 |
| 3,979,669 | 9/1976 | Godin | 324/71 |
| 4,070,617 | 1/1978 | Kachel et al. | 324/71 |
| 4,165,484 | 8/1979 | Haynes | 324/71 |
| 4,253,058 | 2/1981 | Kachel et al. | 324/71 |
| 4,361,803 | 11/1982 | Hogg | 324/71 |
| 4,710,021 | 12/1987 | Von Behrens . | |
| 5,378,633 | 1/1995 | von Behrens et al. | 436/63 |

*Primary Examiner*—Robert Raevis
*Attorney, Agent, or Firm*—Flehr Hohbach Test Albritton & Herbert LLP

[57] ABSTRACT

An apparatus for analyzing particulates including solutes in a sample liquid suspension in which the sample liquid suspension flows through an aperture into a first region of a reservoir containing particle free liquid to form a jet which entrains particle free liquid to ensheathe the jet. The jet passes through a muffler which includes a funnel and a throat into a second region of said reservoir where the particle free liquid and particulates are mixed. The throat is configured to prevent regurgitation of liquid from the second region back into the first region. A return passage connects the second region of the reservoir to the first region. The energy of the jet stream causes liquid to flow from the second region to the first region to provide particle free liquid to the first region. The return passage is configured or contains means to continuously mix the advancing liquid to prevent central streamers and the peripheral Coanda effect. This assures that during particle analysis only clean liquid reaches the first region, and that during cleanout particle free liquid admitted into the first region displaces all analyzed sample liquid without carryover.

9 Claims, 7 Drawing Sheets

FIG_1

FIG_2

FIG_3

FIG_4

FIG_5

FIG_6

FIG_7

FIG_8

FIG_9

FIG_10

FIG_11

FIG_12

FIG_13      FIG_18

FIG_14

FIG_15   FIG_16   FIG_17

FIG_19

METHOD AND APPARATUS FOR ANALYZING PARTICULATE MATTER

REFERENCE TO RELATED APPLICATIONS

This is a continuation of application Ser. No. 08/741,980 filed on Oct. 31, 1996, which claims priority to Provisional Application Serial No. 60/006,917 filed on Nov. 17, 1995.

BRIEF DESCRIPTION OF THE INVENTION

This invention relates generally to a method and apparatus for analyzing particulate matter and more particularly to an improved method and apparatus for obtaining signals from particles or solutes which travel through an aperture and sensing regions without interference from extraneous particulates.

BACKGROUND OF THE INVENTION

There are many types of particle counters. This invention evolved from particle counters of the type commonly known as a Coulter counter. U.S. Pat. No. 2,869,078 describes a counter in which a suspension of particles to be counted flows from an upstream vessel through an aperture to a downstream vessel. An electrical current is established through the aperture by electrodes placed in each of the vessels. The displacement of fluid by a particle in the sensing zone of the sensing aperture causes a change in impedance in this passage. That change in impedance causes a change in current or in voltage which is detected by a suitable detector. The particle laden fluid is caused to flow through the aperture into the downstream vessel by application of a differential pressure such as by withdrawing liquid from the fluid-filled and otherwise closed downstream vessel. The volume of liquid which leaves the closed downstream vessel through an outflow port equals exactly to the volume of liquid traveling through the sensing aperture. By counting the particles as a predetermined volume of fluid leaves the closed downstream vessel, one can obtain the concentration of particles in the particle laden fluid in the upstream vessel.

In the early Coulter particle counters, the downstream vessel quickly became contaminated by analyzed waste and there were no attempts to let only clean fluid reach the sensitive region at the downstream side of the sensing aperture. As a result extraneous particles traveled into that sensing zone and gave rise to extraneous signals and to a buildup of deleterious precipitates. U.S. Pat. No. 3,299,354 provided an additional downstream chamber with an elongated snout having a large capture orifice placed opposite the much smaller sensing aperture. The thin fluid jet formed by the flow of particle laden fluid through the very small sensing aperture was directed into the large capture orifice. The intent was to trap all of the suspended and dissolved particulates. However, according to later patent applications assigned to the assignee of that patent, because of eddy currents and other irregularities, all particulates were not captured by the snout, extraneous counts were still generated at the sensing orifice, and it proved essential to use a burn circuit to keep the rear of the sensing orifice free of particulate precipitates. U.S. Pat. No. 3,746,976 describes an apparatus employing two downstream chambers with an elongated capture snout opposite the sensing aperture. A pump disposed between the two downstream chambers recirculated fluid through a filter to the sensitive zone at the downstream side of the sensing aperture. The action of the pump was to provide clean fluid to hydrodynamically focus the thin particle laden jet from the sensing aperture so that it passed through the first downstream chamber and on through the capture orifice without any of the sample suspension remaining in the region of the sensing aperture, or being able to return to that region. U.S. Pat. No. 4,360,803 is directed to a similar particle analyzing apparatus in which the fluid is allegedly pumped only by the kinetic energy of the thin jet from the sensing aperture and this jet is alleged to be hydrodynamically focused through the large capture orifice. Once one computes the fluidic resistances and pressure gradients in the recirculation circuits and across the capture orifices of any of the structures taught in '803 there is certainly insufficient kinetic energy in the thin jet from the sensing aperture to accelerate the entire merry-go-round cycle through the large capture orifice to beyond the velocity of the incoming jet. Hence, compared with dimensions and velocities of the sample stream jet at the exit of the sensing aperture, there can be no net sample stream acceleration or diameter contraction at the passively functioning cleaning orifice; hence no hydrodynamic focusing. Indeed, despite entrainment of much clean fluid by the thin fluid jet from the small sensing aperture, the resulting expanding, fluttering, ensheathed sample jet is still so small relative to the large capture orifice that it promotes intermittent counter current streams of contaminated fluid to periodically emerge from the capture snout to the sensitive region of the sensing aperture.

The pressure built up in an expansion chamber to create a fluid flow from that chamber is the classic head (static) pressure which also behaves as a backpressure at the entrance to the expansion chamber. This backpressure is well documented in the literature on combustion engines and fan efficiency. In axial fans, it can cause the fluid near the hub to move in the wrong direction through the fan. In the cited particle capture arrangements the head pressure forces waste fluid to flow down the fluctuating pressure field to periodically jet waste contaminants right back out of the "cleaning orifice" and right into the rheologic sump adjacent to the jet emerging from the sensing aperture and within the internal electric fringe field of the "closely spaced" sensing aperture.

U.S. Pat. No. 4,710,021 describes a particulate matter analyzing apparatus in which the original downstream vessel of the Coulter counter is a closed chamber partitioned into two regions, proximal and distal, by a barrier which includes a large capture orifice directly opposite the small sensing aperture formed in the wall of the chamber. The thin sample jet emerging from the small sensing aperture travels through the proximal region of the divided chamber, on through the large capture orifice, and strikes the opposite (distal) chamber wall where it was believed that the kinetic energy was dissipated. However, detailed studies have now shown that as a result of the Coanda surface flow effect, particulate matter rapidly travels along the walls of the distal chamber regions, all faces of the barrier, and the walls of the proximal chamber. Thus particulates and solutes rapidly reach the sensing aperture where they generate extraneous signals and soon disperse throughout the proximal region of the partitioned chamber.

Apparatus exploiting this invention for better resistivity leukocyte analysis has also had to resort to a so-called burn circuit to keep particulate debris from building up in the sensitive region on the downstream side of the sensing aperture. Additionally, Coanda effect contamination throughout the proximal region of the divided chamber has been too high to permit the envisioned exploitation of the region between the sensing aperture and the capture orifice for optical interrogations of the particles or solutes in the thin sample jet.

In addition, because of the necessarily large size of the barrier orifice, there is a tendency for regurgitation of particulates through the orifice via well known countercurrents. Even with the best manufacturing tolerances, a precise axial alignment of the sensing aperture and cleaning orifice can not always be achieved resulting in only a fluttering portion of the sample jet being captured if the capture orifice is made smaller. On the other hand, if the capture orifice is enlarged, this leaves more area for direct regurgitation of particulates driven by the kinetically unopposed head pressure explained above.

OBJECTS AND SUMMARY OF THE INVENTION

It is an object of the present invention to provide an improved analyzing apparatus for analyzing liquid samples carrying suspended particulate matter such as particles or solutes.

It is another object of the present invention to provide an apparatus in which fluid displacement at its inflow or outflow is a measure of the volume traversing each sensor and which apparatus forms a jet stream of sample which travels through a particulate free liquid region where it can be sensed and analyzed.

It is a further object of the present invention to provide a particulate matter analyzing apparatus in which the particulate matter flows through an orifice or aperture to form a jet stream with entrains uncontaminated proximal priming fluid which travels to a distal region which traps the particulate matter and prevents it from interfering with measurements made at the inflow aperture.

It is a further object of the present invention to provide a particulate counter/or analyzer apparatus in which a particulate laden sample fluid intermittently flows from a sensing aperture to form a jet which travels through a particulate free liquid and a high resistance communication path into a dynamic fluid trap so that, through sample containment and energy damping or harnessing in said fluid trap, the region immediately around the sensing aperture is kept clear not only of undesirable fluid dynamics or other fluidically generated energy fields, but also of particles and solutes carried in the particulate laden sample.

It is another object of this invention to provide an apparatus in which samples and reagents are mixed thoroughly in a dynamic fluid trap which they enter in the form of a joint jet.

It is a further object of this invention to provide a reagent primed fluid region into which sample is jetted together with Venturi scavenged priming reagent, through a high-resistance communication path and from which priming reagent can return by a low-resistance return path to satisfy the Venturi needs of the sample jet and in which low-resistance return path neither axial or core streamers nor peripheral or wall-hugging Coanda effect jets can result in macro heterogeneous flow of the leading priming fluid and the following displacement fluid consisting of sample mixed thoroughly with priming fluid.

It is another object of the present invention to provide an apparatus in which all the material in a particulate laden jet is captured in a fluid scavenging and flow rate damping silencer so that a reliably clean and fluidically quiet sensing environment is created for resistivity, optical and other interrogation of particles or solutes carried in the jet.

It is another object of this invention to provide a structure in which tendencies for particles and micro bubbles to accumulate are overcome by a design which facilitates efficient cleanout between every duty cycle.

The foregoing and other objects of the invention are achieved by an apparatus which includes a closed reservoir primed with clean liquid and having an entry aperture which communicates with the first or proximal region to which particulate laden sample fluid flows to form a jet, a muffler, the entry funnel of which is positioned to receive the jet and direct it through a throttling throat into a second or distal region where the concentration of the particulates and the kinetic energy are diluted through efficient mixing and from which region a streamer-preventing and Coanda flow opposing conduit provides a flow of liquid back to the first or proximal region and an exit port allows sample to enter the closed reservoir at the entry aperture by allowing an identical volume of displaced fluid to leave the closed reservoir from the exit port.

BRIEF DESCRIPTION OF THE DRAWINGS

The foregoing and other objects of the invention will be more clearly understood when read in conjunction with the accompanying drawing of which.

DESCRIPTION OF PREFERRED EMBODIMENT

In common with prior art, one embodiment of the present invention counts and analyzes suspended particles by causing a sample suspension to pass through a sensing aperture through which an electric current is also passed. The suspended particles change the impedance through the aperture and modulate the electric current or voltage. Particulates are counted and sized by processing the electric current or voltage. Generally, the particulate containing solution is disposed on one side of the sensing aperture and a clean electrolyte is on the other side of the aperture. A pressure differential causes a predetermined volume of the sample suspension to pass through the aperture and the particulates are counted to give a measure of particulate concentration in the sample. The electrical current or voltage waveform may be analyzed to give an indication of size, shape and composition of the particulates. In other embodiments, the aperture through which the sample fluid is passed is not used as an electrical impedance sensing aperture. Instead, the suspended particles and even solutes in a suspension which may comprise particulates down to the size of molecules are photoelectrically sensed by absorption or reflection of light or by florescence, phosphorescence and analogous interactions of matter with an interrogating energy field through which the unadulterated sample is unidirectionally passed.

Figure 1:
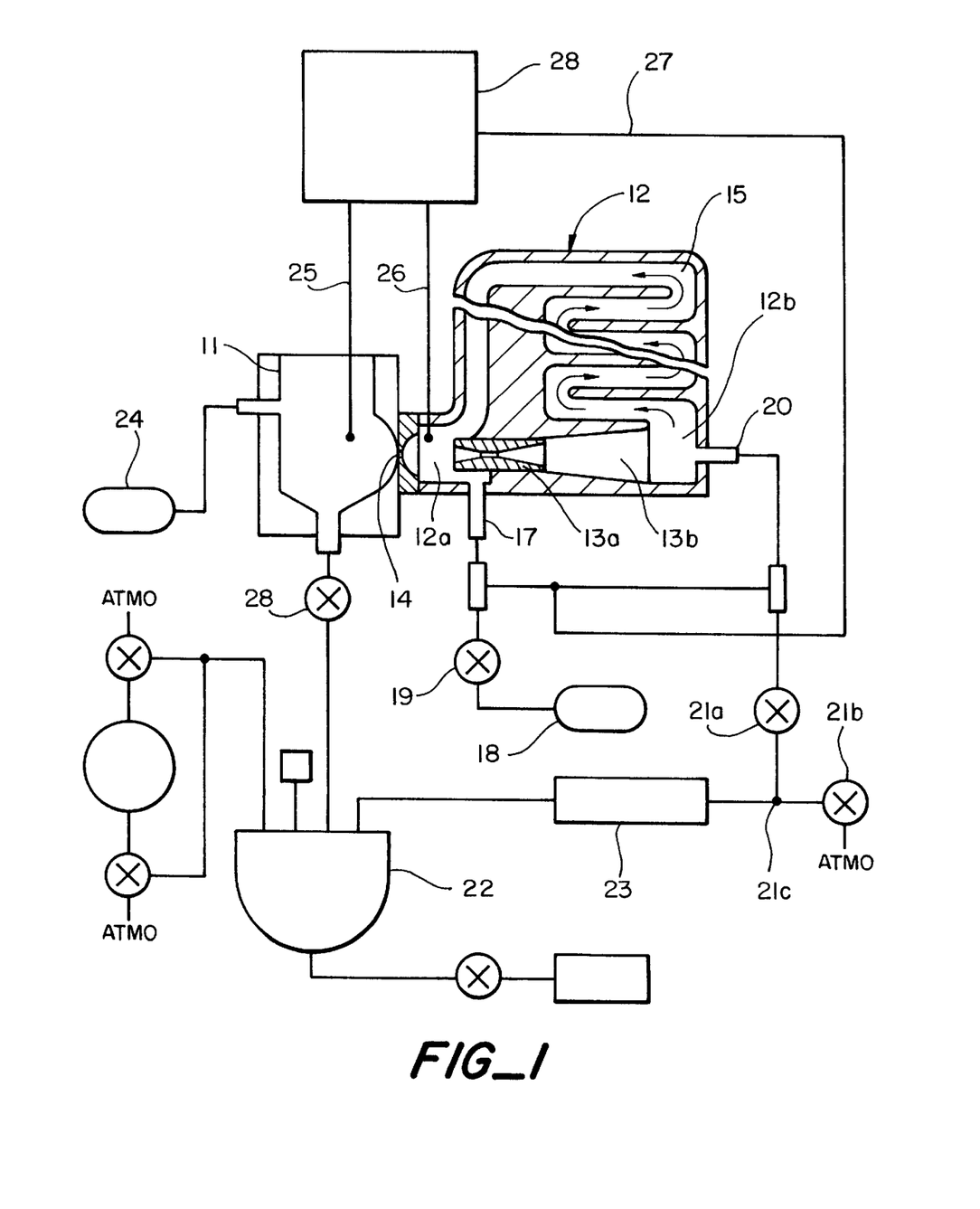
FIG. 1 is a schematic diagram showing a sample cuvette, electrolyte reservoir or chamber, fluid flow control valves and associated system controlling and signal processing electrical circuits.
Figure 2:
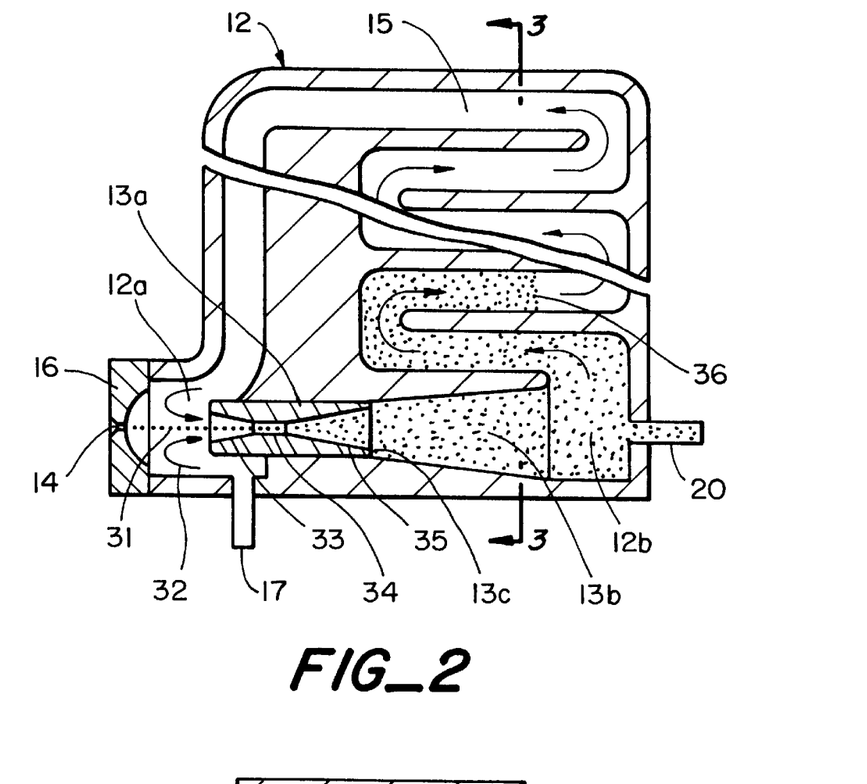
FIG. 2 is an enlarged view showing the electrolyte reservoir or chamber and sensing aperture of FIG. 1.
Figure 3:
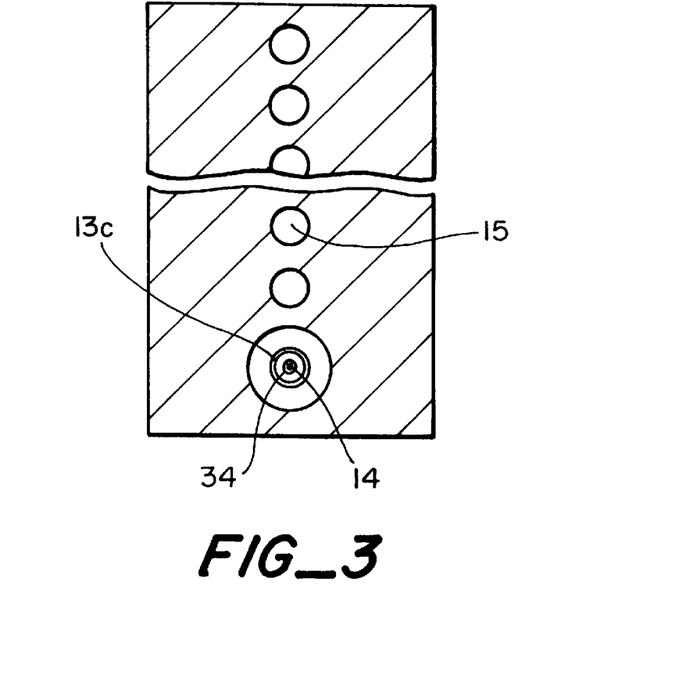
FIG. 3 is a sectional view taken along line 3—3 of FIG. 2.

FIGS. 1–3 show one embodiment of the invention. The sample suspension is received in cuvette 11. An electrolyte reservoir or chamber 12 having proximal region 12a and distal region 12b connected by a muffler 13a,b is coupled to the cuvette 11 through a sensing orifice or aperture 14. An elongated passage 15 acts as a fluid capacitance as part of the fluid reservoir 12 and provides controlled fluid communication between the region 12a and 12b. The region 12a serves as the analyzing region and will be described in more detail hereafter. The passage 15 is a low-resistance return path which counteracts axial streamer formation and surface Coanda flow advances as will be described in more detail later. Together with the muffler 13a,b, and the flow control mechanism built into the fluid conduit 15, the region 12b serves to dynamically trap particulates and to damp and/or harness the kinetic energy of the fluid jet from the analyzing aperture. The aperture 14 may be formed in a jewel 16 which is suitably secured to the body of the reservoir 12. The reservoir or chamber 12 is initially filled with a particulate free or solute free electrolyte or liquid via a fill tube 17 connected to a rinse electrolyte or fluid system 18 via valve 19. The reservoir or chamber 12 is filled and cleaned with clean electrolyte or liquid by opening inlet valve 19 and outlet valve 21a connected to a vacuum reservoir 22 through a volume metering system 23. Valves 19 and 21a are closed after the reservoir is filled with clean electrolyte or priming liquid. The reservoir is designed, in part, as a serpentine conduit to facilitate complete filling without air or bubble entrapment. Valve 21b is now opened momentarily to atmosphere. This introduces an air segment from valve 21b to beyond fluid volume metering manometer 23 leaving a fluid meniscus at the end of the fluid filled line segment from exit port 20 through valve 21a to junction 21c. During this time, the cuvette is filled with the sample suspension from the supply system 24 which can be an automated dilution mechanism for an originally highly concentrated sample like whole blood. Because, during this operating phase, reservoir 12 is a closed fluidic system except at the entry aperture 14 and the exit port 20, when valve 21a is now opened to initiate flow through the sensing aperture 14, stable sample flow is soon established through proximal region 12a as detailed below. During the settling period for this initial flow, a voltage is applied between the electrode 25 disposed in the cuvette and electrode 26 disposed in the chamber region 12a. The voltage across the electrodes causes current to flow through the sensing or analyzing aperture 14. The flowing particulates which modulate this sensing field can therefore be analyzed and counted. Opening the valve 21a to connect the chamber 12 to the vacuum reservoir or source 22 initiates an analytical counting cycle. Liquid is withdrawn from the chamber 12 by the vacuum source 22 into the volume metering system 23 which serves to measure the advance of a predetermined volume of liquid during the flow of which particulates are analyzed and counted passing through the sensing aperture. The metering system 23 may be comprised of photo detectors spaced along a conduit. When a liquid front (not shown but beginning at junction 21c) first reaches a first detector (not shown), counting of particulates is commenced by the signal processing circuit 28 and when the liquid front reaches a second detector (not shown), counting terminates. This general process provides the number of electronically identifiable particles for a given sample volume passing through aperture 14 and region 12a. This sampled volume is equal to the volume of liquid between the photodetectors. After one or more fluid volume measurements, the chamber 12 is cleaned by flushing it with electrolyte from system 18 via valve 19 as described above. The reservoir is thereby also primed with clean electrolyte or diluent, the reservoir having been designed in part as a serpentine conduit to facilitate complete recharging without carryover in the critical fluid regions from prior samples. The sample cuvette is emptied after a sample has been analyzed by opening the valve 28 connected to the vacuum reservoir 22. After the sample is emptied, the cuvette is cleaned by introducing clean electrolyte by further means (not shown). The valve 28 is then closed and new sample suspension is introduced from the sample system 24.

Operation of the apparatus to eliminate interference from extraneous particulate matter in the sensing region will now be explained with particular reference to FIG. 2. When liquid is withdrawn from the closed chamber 12 by opening of the valve 21a, particulate laden sample suspension is drawn through the sensing orifice at a high velocity. This forms a sample jet 31 which travels in a straight line towards the muffler 13. The jet stream 31 entrains clean liquid as indicated by the arrows 32. This accelerating entrained clean liquid ensheathes the jet sample stream 31. The joint jet stream of sample core and surrounding sheath is captured by the conical funnel or muffler entry horn 33 and is constrained or throttled through the narrow throat 34. This joint jet entirely fills the high resistance throat thereby preventing any regurgitation of particulate laden fluid back into the sensing region 12a. Beyond the throat is another horn 35, 13b opening at gradual angle (ideally at subtended half angle below 8°) with optional ribs such as the step shown at the transition 13c from piece 13a to horn continuation 13b. The jet continues into the expansion and mixing region 13b, 12b where the kinetic energy of the core sample jet is dissipated by thoroughly mixing with the particulate free sheath and priming fluid. In other words, by design, muffler 13a is a high-fluidic-resistance passage from region 12a to 12b. The joint jet entering the expansion chamber 12b thereby creates a head pressure while, in the throat and expansion horn 35, 13b, the kinetic impulse of the entering fluid jet prevents direct backflow through the muffler section 13a. This establishes a sustained pressure differential between the regions 12a and 12b so that fluid must flow along the low-fluidic-resistance conduit 15 into the region 12a.

Although the clean and particulate laden fluid mixes intensively in region 12a, it still possesses intense kinetic energy in the form of heterogeneous vorticity. The effect of that is clearly apparent in the fluid front which advances from the exit port into the volume metering manometer 23. Because of the prior cleanout phase after the last sample analysis, fluid segment 20 to 21a can be arranged to commence as totally clean fluid. However, if fluid line 20 to 23 is a typical tube-like conduit, then, even if an additional coiled delay line is inserted between exit port 20 and valve 21a, the waste fluid passing through the manometer is almost instantly contaminated by two dynamic mechanisms, axial core streamers and even thinner peripheral Coanda wall sheet jets. These phenomena are made clearly visible when intensely red anticoagulated whole blood or suitable dyes or inks are used as an indicator sample in cuvette 11. Both the advancing axial core streamers and the rapidly moving surface sheets can only occur through the concurrent formation of analogous countercurrent flows of, initially, clean priming fluid. It is irrelevant to the manometer's function that during the commencement of an analytical cycle, the initially clean fluid limb 20 to 21c rapidly becomes contaminated during passage of its leading meniscus from location 21c to 23.

If conduit 15 were a simple fluid conducting tube, whether straight or smoothly coiled, then during the commencement of an analytic counting cycle, proximal region 12a of fluid reservoir 12 would also rapidly become contaminated from distal region 12b through the mechanisms of leading axial core streamers and advancing peripheral Coanda surface sheets. This fact is made clearly visible if, for low-fluidic-resistance conduit 15, a smooth coil of equal length or capacity and fluid resistance is substituted in the structure of FIGS. 1–3 or FIGS. 4–6 and then undiluted whole blood or India ink is used as an indicator sample in cuvette 11. An essential key to this invention is that the conduit 15 is designed to inhibit or control along its course both of these discovered heterogenising mechanisms, axial core streamers and peripheral Coanda effects. The conduit is characterized by numerous acute but smooth-contoured switchbacks. Additionally, the alternate short straight runs of conduit 15 which are shown in section in FIG. 3 can be staggered laterally in the Z direction of FIG. 2 with left right alternation to induce further vorticity homogenizing effects across the overall serpentine direction of flow through conduit 15. On top of that, readily available counter turning complimentary alternating fluid mixing inserts 40, such as Statomix® units, can be introduced into the entire length of the low fluid resistance conduit 15. As a result, instead of piercing axial or peripheral advance jets, a uniform particulate laden front 36 travels along the conduit or passage 15.

Well before the front 36 reaches the area adjacent to the clean proximal region 12a the cleaning or washing phase of the operational cycle is commenced as described above. Both the switchback anti-demixing design of loop 15 in FIGS. 1–3 and the in-line mixing inserts retain their anti-demixing characteristics when flow is reversed for cleaning.

Thus, the present invention permits frugal, fluidically quiet, self ballasting delivery of fresh downstream fluid into a post restriction transducer region 12a. The invention overcomes the need to place interfering rigid physical boundaries into the immediate post restrictor region or to continuously or periodically deliver very large volumes of fresh liquid into that region. The present invention captures all of the material carried by a post constriction sample jet in the region downstream of the entry to the capture horn 33 of a miniaturized fluid scavenging silencer so that in region 12a, a reliably clean and fluidically quiet and stable sensing environment is created for resistivity, optical or other interrogation of particulates or solutes carried in the jet. Concurrently, a volume of fluid equivalent to that entering the proximal region 12a in the form of the sample jet 14 leaves distal region 12b through exit port 20.

Figure 4:
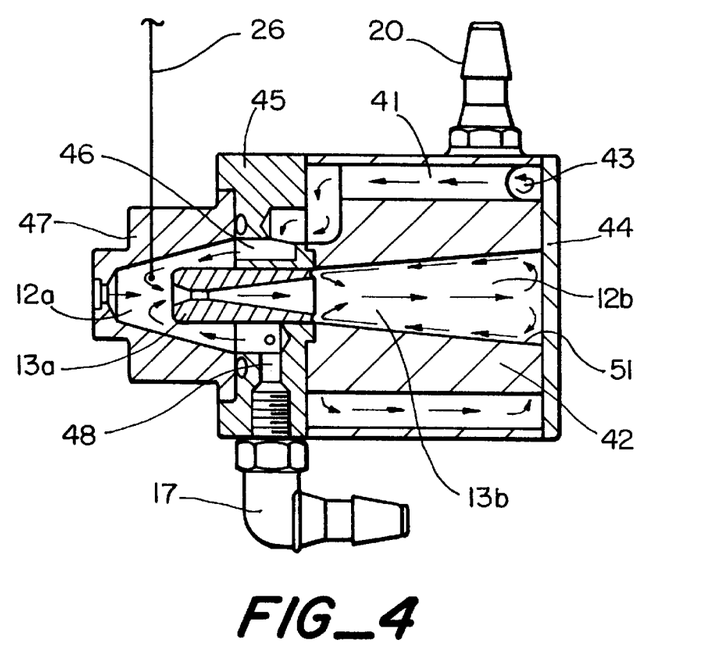
FIG. 4 is a sectional view of another embodiment of an electrolyte reservoir and sensing aperture showing the flow of electrolyte and suspended particulates during the analytical counting phase of an operating cycle.
Figure 5:
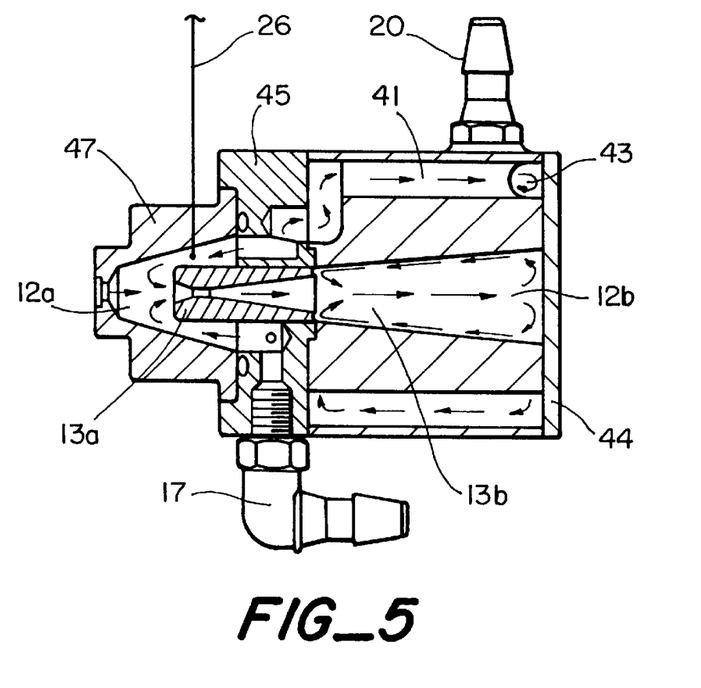
FIG. 5 is a sectional view of the reservoir of FIG. 4 showing flow of clean electrolyte during the phase of the operating cycle when the aperture and electrolyte reservoir are cleaned and primed for analysis of the next sample.
Figure 6:
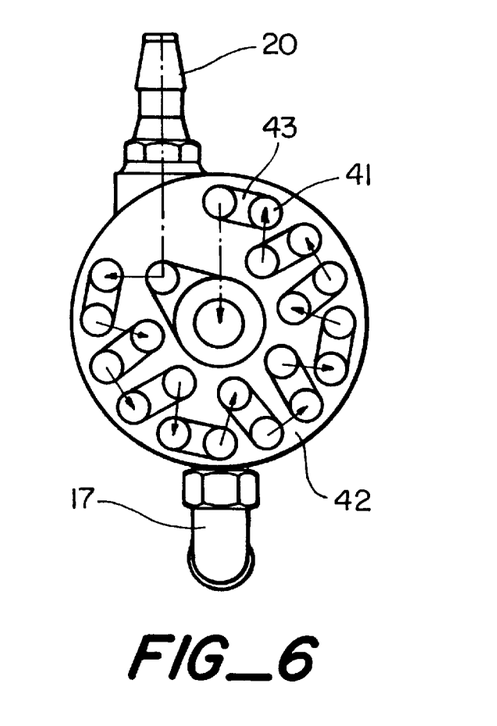
FIG. 6 shows an end view of the apparatus shown in FIGS. 4 and 5 looking through a transparent end cover.

FIGS. 4–6 illustrate another embodiment of the closed chamber. The chamber is formed by drilling a plurality of passages 41 in a cylindrical solid member 42 with cross passages 43 providing communication between the adjacent ends of selected pairs of passages 41 so that a single continuous serpentine conduit is created without short-circuiting possibilities. A cover 44 is applied to one end and a machined cover 45 is applied to the other end. Thus, the covers 44, 45 cooperate with the cross passages of the cylinder to form an intensely reflexing continuous low-resistance passageway connecting regions 12a and 12b. The cover 45 includes first passage 46 for introduction of scavenged clean fluid into the sensing region 12a formed between the jewel mounting member 47 and the protruding nozzle of muffler 13a. Second passage 48 provides communication to the valve 19 for the priming and washout supply of clean fluid after counting cycles. The cylindrical member includes a conical bore 51 which represents expansion chamber 13b and mixing chamber 12b. The arrows in FIG. 4 show the flow of liquid during a measuring phase of the instrument whereas FIG. 5 shows the flow of liquid during a cleaning or filling phase. Operation of the analyzing cell, FIGS. 4–6, is the same as described in reference to FIG. 2. That is, the particle laden jet is ensheathed with clean fluid and travels into the funnel 33 through the narrow, high-fluid-resistance throat 34 through expansion horn 35 over ribs 36, through continuation of the expansion horns 13b and into the head pressure capacitor region 12b. The conduit 15 inhibits or controls axial core streamers and peripheral Coanda effects as described with reference to FIGS. 1–3.

Figure 7:
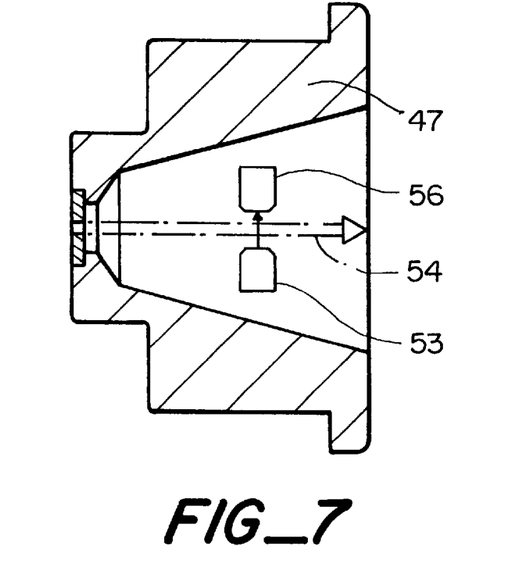
FIG. 7 shows a photo-electric sensor for sensing of particulates in the clean sample jet stream.
Figure 8:
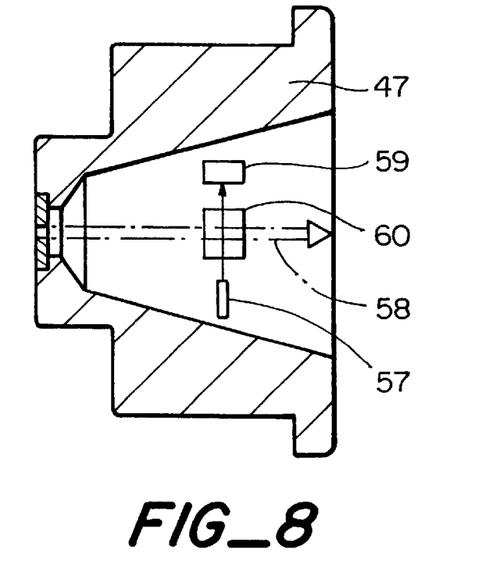
FIG. 8 shows a laser beam and transducers for analyzing particulates in the clean sample jet stream.

Referring to FIG. 7, there is shown a photodiode 53 which shines light through the particle laden jet 54 with the light being received by a photodetector 56. The photo diode-photodetector combination senses and counts particulates in the jet stream. FIG. 8 shows a laser 57 shining light into the jet stream 58 with the photodetector 59 receiving transmitted light to indicate absorption by particulate matter whereas the detector 61 senses light reflected by particulate matter and a diametrically opposed detector senses fluorescence excited by the laser 57 and emitted by the particulate matter. The laser may operate at a predetermined wavelength and the particles may be tagged selectively to fluoresce in response to the light as they travel through the laser beam.

Operation of the apparatus will now be described with reference to one analytical counting cycle. Before a count commences, clean fluid is caused to fill the entire fluid region of the chamber 12 which as in FIG. 1, is bounded by entry aperture 14, cleanout valve 19 and exit line valve 21a. When samples are processed continuously without long interruptions between analysis, a "miser mode" of operating the system can be selected and even less priming fluid is necessary. After the system is primed, valve 21b is opened briefly to establish the fluid meniscus at junction 21c to facilitate the metering mechanism 23. The sample cuvette 11 is charged with the known dilution of sample. The valve 21a is then opened and the orifice jet starts to flow due to the applied differential pressure across the sensing orifice 14. This initiates the jet flow from the orifice into the capture funnel 33, through the high-fluid-resistance (choking) throat 34 and into the expansion horn, kinetic energy diffuser and mixing region 35, 13b, 12b. In one example, the strong sample jet, flowing at 15 μl/s, carries with it some 91 μl/s of pristine fluid through the throat. As the air-fluid interface meniscus at junction 21c advances towards the volume metering system 23 current is applied to electrode 26 as in the description of FIGS. 2 and 3. Volumetric metering during the counting phase of the analytic cycle may be by photosensors. Counting of particulates in a known volume of fluid is initiated by the advancing meniscus triggering one of potentially many "start sensors" and terminated when the meniscus reaches any one of potentially many "stop sensors". The volume of flowing fluid which was needed to advance the meniscus between sensors from any start to any stop sensor has been calibrated previously and is thereby known very precisely. Since the start and stop meniscus and sensors are similar to each other, the systematic differences which result from ambient temperature changes do not affect this calibration even though the viscosity of water changes enormously from cold to warm laboratory environments for an instrument. Since the sensing orifice is, in fact, a capillary viscometer, the precisely measured count time reflects this viscosity. However, the manometer volume is independent of this. Provided the rigorously monitored system remains stable in pressure and flow, multiples of the currently measured count time therefore provide precisely extrapolated volume multiples below and above the calibration volume represented by the manometer volumes. A 100 μl manometer therefore permits "volumetric metering" from, say, 10 μl to over 1000 μl provided the entry aperture conditions are immune to flow restricting deposits from the accumulating waste inflow.

During the counting phase of a 330 μl manometer analytic cycle: 2330 μl of fluid flows through the chocking muffler throat into the expansion chamber, and out of the expansion chamber into the metering and recirculation lines; 330 μl of sample fluid flows through the entry aperture 14, through the clean sensing region 12a as sample jet, through the muffler as sample accompanied by 2000 μl of scavenged clean Venturi fluid, from the exit port 20 as sample waste extensively diluted by the priming and sheath fluids, and from the manometer's start sensor to the manometer's stop sensor as a front commencing as clean priming fluid which is however quickly contaminated by axial core streamers in combination with Coanda wall sheets of mixed waste darting ahead from exit port 20; 2000 μl of fluid also flows from the expansion chamber at 12b into the 4,320 μl capacity recirculation cyclo-labyrinth or conduit 15 where it is maintained in the form of well-compacted waste, thereby displacing 2000 μl of clean fluid into the chamber portion 12a.

Within the cyclo-labyrinth, the inherent tendency for axial streamers and Coanda surface jets to shoot continuously ahead in a straighter conduit and to rapidly penetrate to 12a is counteracted by the intense curl and accompanying vorticity which are added by the controlled reflexive folding and acute serpentine twisting of the passages even without insertion of any additional available mixing elements. In traversing this compact labyrinth 41, FIGS. 4–6, an element of fluid undergoes continuous homogenization synchronization of mean velocity with adjacent elements of fluid in any cross section by executing around 10 three hundred and sixty degree revolutions in the cross-sectional plane and some 5 complete three hundred and sixty degree revolutions in the longitudinal plane. It is unnecessary to argue over whether or not true turbulent flow is established anywhere in this system. Relative homogeneity of the advancing front is readily demonstrated with the described indicator techniques which also demonstrate the failure of prior attempts to solve this problem.

During the cleanout phase of the analytic cycle, as illustrated in FIGS. 1 and 5, the muffler flows remain in the same direction, but the flows in the cyclo-labyrinth are reversed. The anti-demixing design also functions under reverse flow and, because the inflow of cleanout fluid is through the macro-port instead of the micro-orifice, the orderly cleanout is vigorous and rapid.

Figure 9:
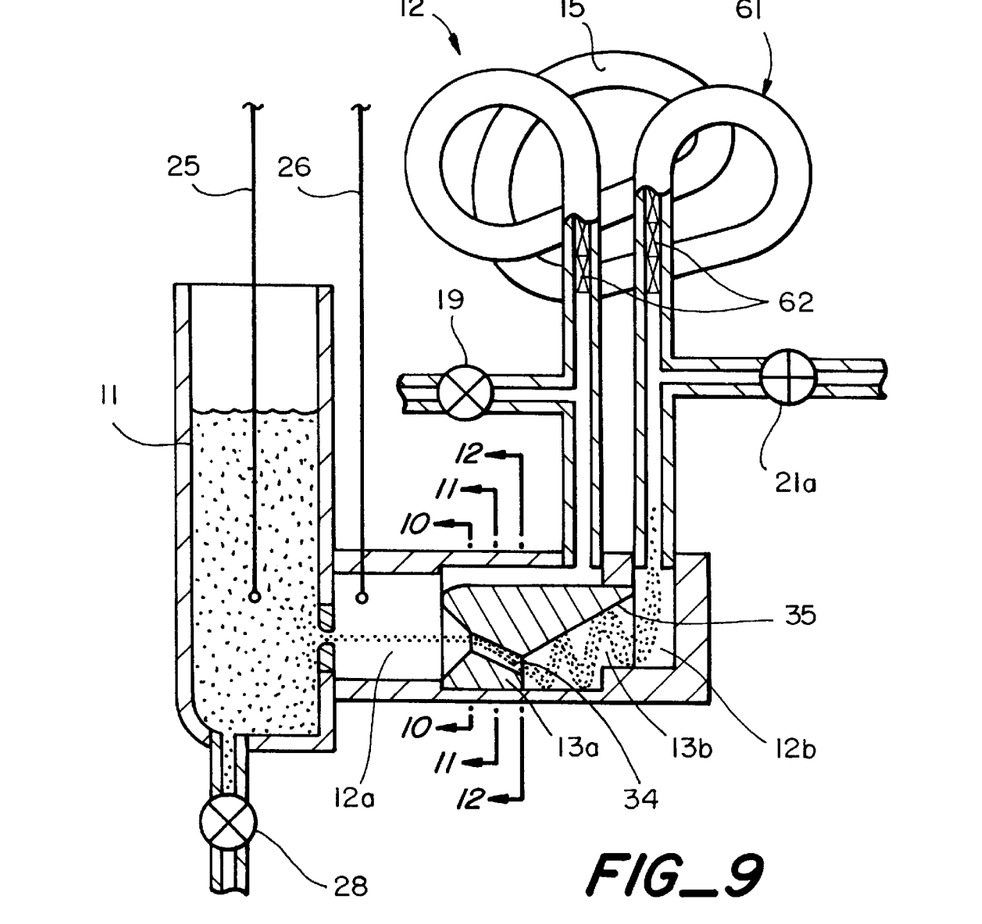
FIG. 9 is a sectional view of another embodiment of the invention showing a sample cuvette and an electrolyte reservoir with controlled flow of priming electrolyte and suspended particulates during a counting cycle.
Figure 10:
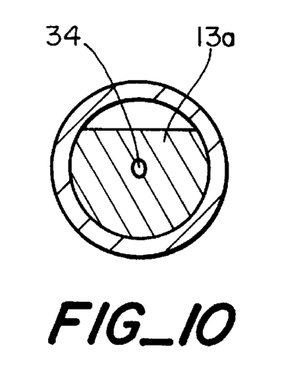
FIG. 10 is a sectional view taken along the line 10—10 of FIG. 9.
Figure 11:
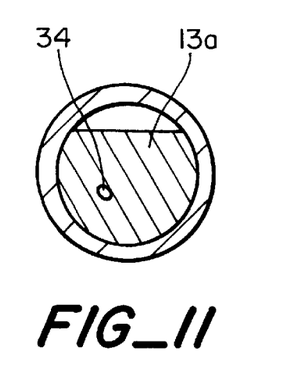
FIG. 11 is a sectional view taken along the line 11—11 of FIG. 9.
Figure 12:
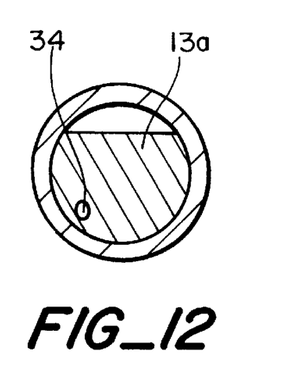
FIG. 12 is a sectional view taken along the line 12—12 of FIG. 9.
Figure 13:
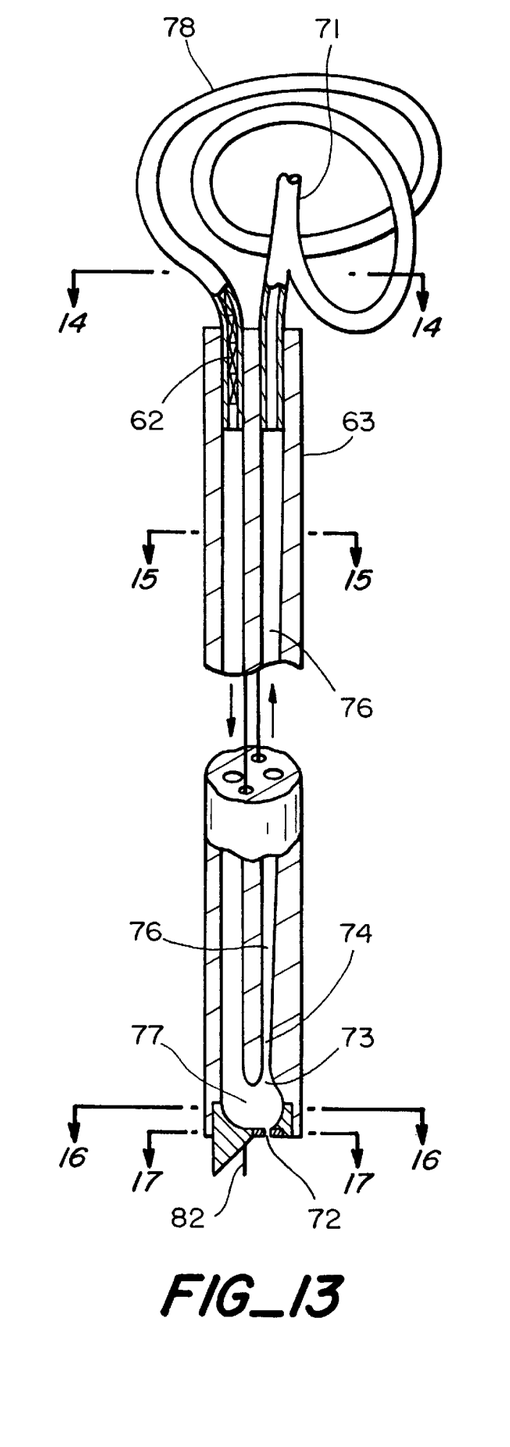
FIG. 13 shows a sensing aperture tube embodiment of the invention.
Figure 14:
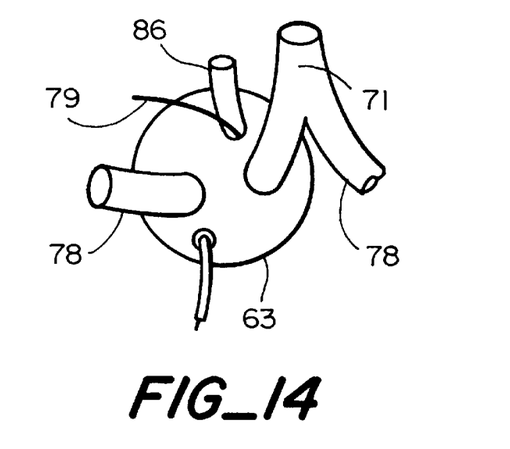
FIG. 14 is a top plan view taken along the line 14—14 of FIG. 13.
Figure 15:
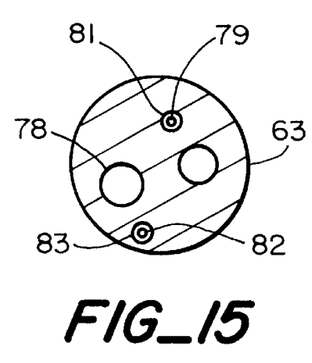
FIG. 15 is a sectional view taken along the line 15—15 of FIG. 13.
Figure 16:
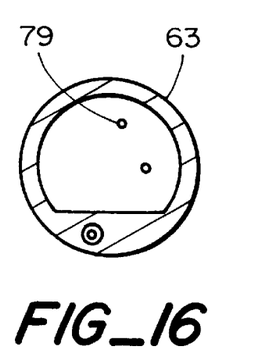
FIG. 16 is a sectional view taken along the line 16—16 of FIG. 13.
Figure 17:
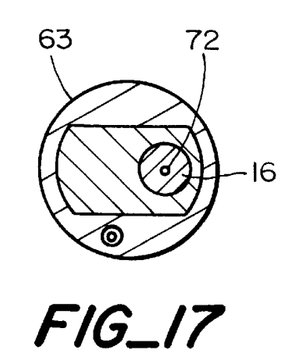
FIG. 17 is a sectional view taken along the line 17—17 of FIG. 13.

Referring to FIGS. 9–12, there are shown sectional views of another particulate matter sensing apparatus. Like reference numerals have been applied to the like parts. The apparatus includes a cuvette 11, a chamber 12 including regions 12a, 12b, interconnected by low-fluid-resistance conduit 15, in the form of a tube 61. Cleaning valves 19 and exhaust valves 21a are shown connected to the reservoir portions 12a and 12b respectively. In the embodiment of FIG. 9, the fluidic mixing and kinetic energy absorption at the silencer diffusion or mixing region 12b is enhanced by forming the high-fluid-resistance throat in the muffler at an angle whereby to impart a circular vortex motion in the expansion horn 35, 13b as the sheath-laden sample jet stream progresses to region 12b. FIGS. 10, 11 and 12 illustrate progressive deviation of the throat passage through 13a from the center to the side which imparts the circular vortex or rotational impetus. However, in gradually curved tubing loops of the conduit, like those illustrated in FIG. 9, it is necessary to insert the mixing elements 62, such as Statomix® units, along the tube to prevent axial streamers and peripheral surface sheet advances. In other respects, the embodiments of FIGS. 9–12 operate as previously described.

FIGS. 13–17 show a further embodiment of the invention incorporated in a tube 63 whose lower end is immersed into a beaker or cuvette (not shown) containing the particulate laden sample which is to be analyzed. Fluid is drawn from the closed system via the tube 71. As fluid is withdrawn, particle laden sample is drawn through the orifice 72 to form a jet which impinges upon the funnel 73, travels through the choking throat 74 and into the expansion or mixing chamber 76 where kinetic energy is dissipated and mixing takes place. Clean fluid circulates to the analyzing region 77 via low-fluid-resistance conduit 78 which includes mixing elements 62 as previously described. One sensing electrode 79 extends along the fluid carrying passage 81 into the region 77. The other sensing electrode 82 extends along the sealed passage 83 into the beaker or cuvette. A cleaning cycle is initiated by supplying fluid through the tube 86 and passage 81 as the fluid is withdrawn through the tube 71.

Figure 18:
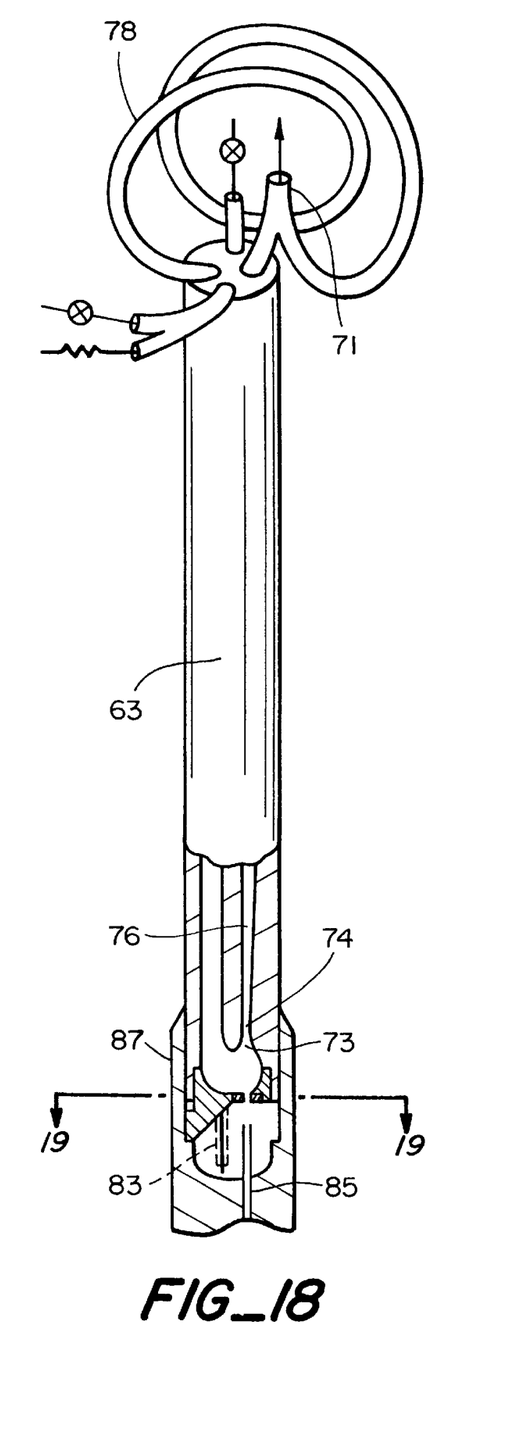
FIG. 18 shows another sensing aperture tube embodiment of the invention.
Figure 19:
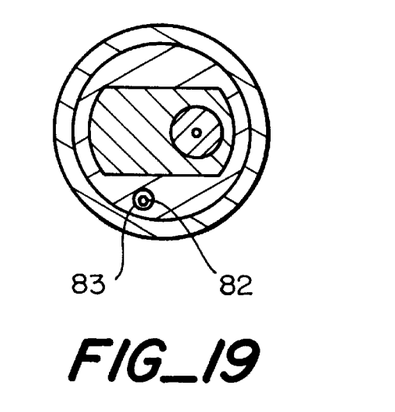
FIG. 19 is a sectional view taken along the line 19—19 of FIG. 18.

FIG. 18 shows the same analyzing apparatus with a front focusing cap 87. The cap carries a capillary tube 85 which is a fluidic resistor and releases the particle laden fluid into the entry flow net of the sensing orifice. Passage 83 of FIG. 18 now carries both the electrode 82 and sheath fluid for hydrodynamically focusing the sample stream from capillary through the sensing orifice.

What is claimed is:

1. An apparatus for analyzing particulates including solutes in a sample liquid suspension comprising:
  a sample liquid reservoir for containing said liquid suspension;
  a particulate free liquid reservoir including a first or proximal region and a second or distal region forming a diffusion or expansion chamber;
  an aperture in said particulate-free reservoir for coupling said sample liquid reservoir to said particulate-free liquid in said first proximal region;

a low-fluid-resistance passage for storing fluid, conveying fluid between said first region and second regions, and configured to induce vorticity in fluid flowing through said passage to counteract axial streamer formation and surface Coanda flow;

a muffler including a jet-containing entry funnel and a long, narrow throttling throat disposed in line with the axis of said aperture for connecting the first region to the second region; and, an exhaust port connected to said particulate free liquid reservoir whereby when liquid is exhausted from said reservoir through said port, particulate laden liquid flows through said aperture from said sample liquid reservoir and forms a high velocity jet which entrains particulate free liquid from said first region and travels ensheathed with particle free liquid through said jet-containing entry funnel and long, narrow throttling throat into the second region where the kinetic energy of said ensheathed jet thoroughly mixes the particulate free liquid sheath and the particulate laden liquid suspension, said ensheathed high velocity jet guided by the entry funnel into the long, narrow throttling throat into said second region also providing a unidirectional pressure differential between said second and said first regions so that particulate free priming fluid is displaced progressively and evenly by the mixture from the second region through the vorticity inducing fluid passage to said first region, and the particulate-laden mixture can neither regurgitate through said muffler to said first region, nor advance as a thin axial streamer or thin surface Coanda sheet through said low fluid resistance passage to said first region.

2. An apparatus as in claim 1 which includes one or more sensors for counting particulates flowing from the sample liquid reservoir into said apparatus.

3. An apparatus as in claim 2 in which one of the sensors includes said aperture through which particle detection current flows.

4. An apparatus as in claim 2 in which at least one of the sensors is an optical sensor placed downstream from the aperture for coupling the particle free reservoir to the sample liquid reservoir.

5. An apparatus as in claim 4 in which the optical sensor measures the fluorescence of labeled particulates.

6. An apparatus as in claim 5 in which the optical sensor measures light scattered by particulates.

7. An apparatus as in claim 1 in which said muffler includes an exit cone at said long, narrow throttling throat.

8. An apparatus for analyzing particulates including solutes in a sample liquid suspension comprising:

a reservoir for containing said liquid suspension;

a particulate free liquid reservoir including a first or proximal region and a second or distal region forming the diffusion or expansion chamber of a silencer;

an aperture for coupling the particulate-free liquid in the first proximal region of said reservoir to said sample liquid suspension;

a low-fluid-resistance passage for storing and conveying fluid between said first region and said second region; and, a muffler including a jet entry funnel and a long, narrow throttling throat disposed inline with the axis of said aperture for connecting the first region to the second region; and means for flowing sample liquid suspension through said aperture to form a high velocity jet which entrains particle free liquid from said first region, entirely fills the throat, and travels ensheathed with the particle free liquid through said jet-capturing muffler funnel and long, narrow throttling throat into the second region where the kinetic energy of said jet is dissipated by thoroughly mixing the particulate free liquid sheath and the particulate laden liquid suspension, said dissipation of kinetic energy of the high velocity jet resulting in a static head pressure differential across the muffler between said second region and said first region, said ensheathed high velocity jet entering and filling said long, narrow throttling throat, blocking regurgitation of particles from said second region to the first region, said ensheathed high velocity jet entering the second region thereby providing a uni-directional pressure differential between said first and second regions so that particulate free priming fluid is displaced progressively from the second region through the fluid passage to the first region.

9. The method of analyzing particulates including solutes in a sample liquid suspension comprising the steps of:

jetting a sample fluid suspension into a first region having particle free liquid to ensheathe said jet in said particle free liquid; and, directing said ensheathed particle jet into an entry funnel which directs the fluid through a long constricted throttling throat to entirely fill the throttling throat to completely occlude the return of fluid, and into an expansion region where the kinetic energy of said jet thoroughly mixes the particulate free liquid sheath and the particulate laden liquid suspension, said ensheathed jet leaving said long constricted throttling throat providing a unidirectional pressure differential between the first and second regions so that particulate free priming fluid is displaced progressively by the mixture from the second region through a fluid passage to said first region.

* * * * *